(12) United States Patent
Wakamatsu et al.

(10) Patent No.: US 11,760,724 B2
(45) Date of Patent: *Sep. 19, 2023

(54) PYRIDONE COMPOUND PRODUCTION METHOD

(71) Applicant: SUMITOMO CHEMICAL COMPANY, LIMITED, Tokyo (JP)

(72) Inventors: Takayuki Wakamatsu, Takarazuka (JP); Miyuki Iguchi, Takarazuka (JP); Junichi Ishikawa, Takarazuka (JP); Tohru Inoue, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 286 days.

This patent is subject to a terminal disclaimer.

(21) Appl. No.: 17/426,431

(22) PCT Filed: Jan. 29, 2020

(86) PCT No.: PCT/JP2020/003087
§ 371 (c)(1),
(2) Date: Jul. 28, 2021

(87) PCT Pub. No.: WO2020/158773
PCT Pub. Date: Aug. 6, 2020

(65) Prior Publication Data
US 2022/0106273 A1 Apr. 7, 2022

(30) Foreign Application Priority Data
Jan. 30, 2019 (JP) .................. 2019-013999

(51) Int. Cl.
*C07D 213/89* (2006.01)
*C07D 213/69* (2006.01)

(52) U.S. Cl.
CPC .......... *C07D 213/69* (2013.01); *C07D 213/89* (2013.01)

(58) Field of Classification Search
CPC ............................ C07D 213/89; C07D 213/69
See application file for complete search history.

(56) References Cited

U.S. PATENT DOCUMENTS

| | | | |
|---|---|---|---|
| 3,846,553 A | 11/1974 | Shen et al. | |
| 6,537,948 B1 | 3/2003 | Tohyama et al. | |

FOREIGN PATENT DOCUMENTS

| | | |
|---|---|---|
| JP | 2002-155061 A | 5/2002 |
| WO | WO 2007/083090 A2 | 7/2007 |

OTHER PUBLICATIONS

International Preliminary Report on Patentability and Written Opinion of the International Searching Authority for International Application No. PCT/JP2020/003087, dated Jul. 27, 2021.

(Continued)

*Primary Examiner* — Timothy R Rozof
(74) *Attorney, Agent, or Firm* — Birch, Stewart, Kolasch & Birch, LLP

(57) ABSTRACT

The present invention provides an effective production method for a pyridone compound. More specifically, the present invention provides a production method comprising: a step of reacting the compound represented by formula (1) (in the formula, $X^1$ and $X^2$ each independently represent a halogen atom, $R^1$ represents a hydrogen atom, an amino group, or a group represented by $NHCOR^2$, and $R^2$ represents a C1-C5 alkyl group) with 4 to 10 times by mass, with respect to the compound represented by formula (1), of the compound represented by formula (2) (in the formula, $R^2$ represents the same as described previously), in the presence of at least one of a tri(C1-C8 alkyl)amine and an alkali metal acetate, at a temperature of 100° C. or higher to obtain the compound represented by formula (3) (in the formula, $X^1$, $X^2$ and $R^2$ represent the same as described previously, $R^6$ represents a hydrogen atom or an $NHCOR^2$ group); and a step of hydrolyzing the compound represented by formula (3), to obtain the pyridone compound represented by formula (4) (in the formula, $X^1$, $X^2$ and $R^1$ represent the same as described previously).

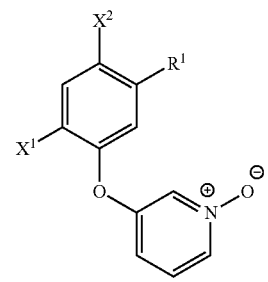

(1)

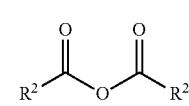

(2)

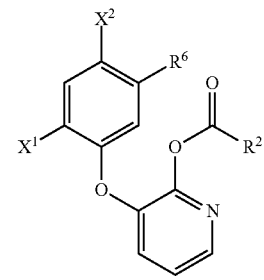

(3)

(Continued)

-continued

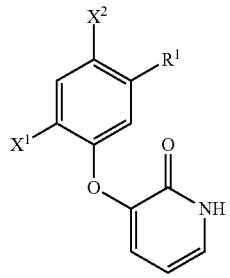

(4)

11 Claims, No Drawings

(56) References Cited

OTHER PUBLICATIONS

International Search Report for International Application No. PCT/JP2020/003087, dated Mar. 31, 2020.
Indian Office Action for Indian Application No. 202117033948, dated Feb. 24, 2023, with English translation.

PYRIDONE COMPOUND PRODUCTION METHOD

TECHNICAL FIELD

This application claims priority to and the benefit of Japanese Patent Application No. 2019-013999 filed on Jan. 30, 2019, the entire contents of which are incorporated herein by reference.

The present invention relates to a method for preparing a pyridone compound.

BACKGROUND ART

Patent Document 1 describes a uracil compound which is useful as a herbicide. Patent Document 2 describes a method for preparing the above uracil compound, and discloses that a compound represented by formula (4):

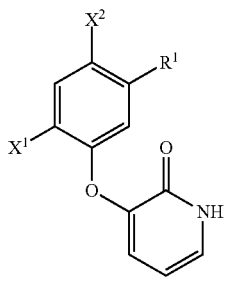

(4)

[wherein, $X^1$ and $X^2$ each independently represent a halogen atom, $R^1$ represents a hydrogen atom, an amino group or a group represented by $NHCOR^2$, and $R^2$ represents a C1-C5 alkyl group]
(hereinafter, referred to as "compound (4)") is useful as an intermediate compound for producing a herbicide.

CITATION LIST

Patent Document

Patent Document 1: U.S. Pat. No. 6,537,948 B1
Patent Document 2: WO2007/083090 A2

SUMMARY OF THE INVENTION

Problems to be Solved by Invention

However, the method described in Patent Document 2 shows a low yield of the compound (4), and is not necessarily satisfied as a preparation method.

An object of the present invention is to provide an efficient method for preparing the compound (4).

Means to Solve Problems

The inventors of the present invention have completed the present invention as a result of intensive studies to solve the above problems.

The present invention is as follows.
[1] A method for preparing a compound represented by formula (4):

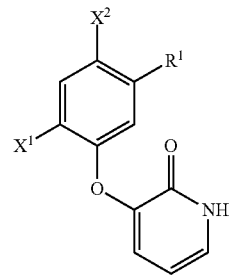

(4)

[wherein, $X^1$ and $X^2$ each independently represent a halogen atom, $R^1$ represents a hydrogen atom, an amino group or a group represented by $NHCOR^2$, and $R^2$ represents a C1-C5 alkyl group]
which comprises a step (B) a step of reacting a compound represented by formula (1):

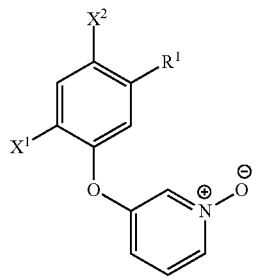

(1)

[wherein, $X^1$, $X^2$ and $R^1$ have the same meanings as described above]
with a compound represented by formula (2):

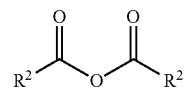

(2)

[wherein, $R^2$ has the same meaning as described above]
which is 4 to 10 times by weight as much as the compound represented by formula (1), in the presence of at least one of a tri(C1-C8 alkyl)amine and an alkali metal acetate at a temperature of 100° C. or higher to obtain a compound represented by formula (3):

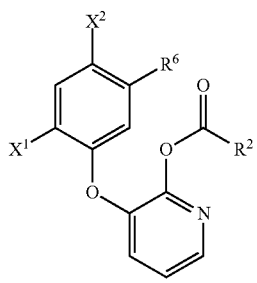

(3)

[wherein, $X^1$, $X^2$ and $R^2$ have the same meanings as described above, and $R^6$ represents a hydrogen atom or a group represented by NHCOR$^2$]; and a step (C): a step of hydrolyzing the compound represented by formula (3) to obtain the compound represented by formula (4).

[2] The method according to [1], wherein the tri(C1-C8 alkyl)amine is triethylamine, diisopropylethylamine or tri-octylamine.

[3] The method according to [1], wherein the alkali metal acetate is sodium acetate.

[4] The method according to [1], wherein the at least one of tri(C1-C8 alkyl)amine and alkali metal acetate includes a tri(C1-C8 alkyl)amine.

[5] The method according to [1], wherein the at least one of tri(C1-C8 alkyl)amine and alkali metal acetate includes an alkali metal acetate.

[6] The method according to [4], wherein the tri(C1-C8 alkyl)amine is triethylamine, diisopropylethylamine or tri-octylamine.

[7] The method according to [5], wherein the alkali metal acetate is sodium acetate.

[8] A method for preparing a compound represented by formula (4):

(4)

[wherein, $X^1$ and $X^2$ each independently represent a halogen atom, $R^1$ represents a hydrogen atom, an amino group or a group represented by NHCOR$^2$, and $R^2$ represents a C1-C5 alkyl group]

which comprises a step (A) a step of reacting a compound represented by formula (5):

(5)

[wherein, $X^3$ represents a halogen atom] with a compound represented by formula (6):

(6)

[wherein, $X^1$, $X^2$ and $R^1$ have the same meanings as described above]

in the presence of a base to obtain a compound represented by formula (1):

(1)

[wherein, $X^1$, $X^2$ and $R^1$ have the same meanings as described above]; and the step (B) and the step (C) described in any one of [1] to [7].

[9] The method according to any one of [1] to [8], wherein $X^1$ represents a chlorine atom.

[10] The method according to any one of [1] to [9], wherein $X^2$ represents a fluorine atom.

[11] A compound represented by formula (3):

(3)

[wherein, $X^1$ and $X^2$ each independently represent a halogen atom, $R^2$ represents a C1-C5 alkyl group, and $R^6$ represents a hydrogen atom or a group represented by NHCOR$^2$].

Effect of Invention

According to the present invention, the compound (4) can be prepared in high yield.

MODE FOR CARRYING OUT THE INVENTION

The present invention is described in detail below.

The step (B) is described below.

In the step (B), the compound represented by formula (1) (hereinafter, referred to as "compound (1)") is reacted with the compound represented by formula (2) (hereinafter referred to as "compound (2)"), which is 4 to 10 times by weight as much as the compound represented by formula (1), in the presence of at least one of a tri(C1-C8 alkyl)amine and an alkali metal acetate at a temperature of 100° C. or higher to obtain the compound represented by formula (3) (hereinafter, referred to as "compound (3)").

Examples of the C1-C5 alkyl group of $R^2$ include methyl group, ethyl group, propyl group, isopropyl group, butyl group, isobutyl group, sec-butyl group, tert-butyl group and pentyl group, include preferably methyl group or ethyl group, and more preferably methyl group.

$X^1$ preferably represents a chlorine atom. $X^2$ preferably represents a fluorine atom. $R^1$ preferably represents a hydrogen atom. The compound (1) wherein $X^1$ represents a chlorine atom, $X^2$ represents a fluorine atom and $R^1$ represents a hydrogen atom is referred to as 3-(2-chloro-4-fluorophenoxy)pyridine-N-oxide.

Alternatively, $R^1$ may represent an amino group ($NH_2$). The compound (1) wherein $X^1$ represents a chlorine atom, $X^2$ represents a fluorine atom, and $R^1$ represents an amino group is referred to as 3-(5-amino-2-chloro-4-fluorophenoxy)pyridine-N-oxide.

$R^6$ preferably represents a hydrogen atom. The compound (3) wherein $X^1$ represents a chlorine atom, $X^2$ represents a fluorine atom, $R^6$ represents a hydrogen atom, and $R^2$ represents a methyl group is referred to as 2-acetoxy-3-(2-chloro-4-fluorophenoxy)pyridine.

Here, examples of halogen atoms include fluorine atom, chlorine atom, bromine atom, and iodine atom.

The compound (2) is preferably an acetic anhydride. Acetic anhydride corresponds to the compound (2) wherein $R^2$ represents a methyl group.

It is preferable to carry out the reaction at 100° C. to 140° C. using the acetic anhydride as the compound (2). It is more preferable to carry out the reaction at 110° C. to 140° C. using the acetic anhydride as the compound (2). It is particularly preferable to carry out the reaction at 120° C. to 140° C. using the acetic anhydride as the compound (2).

The amount of the compound (2) to be used is 4 to 10 times by weight, and preferably 5 to 10 times by weight, as much as the amount of the compound (1).

Although in the reaction it is possible to use a compound represented by formula (8):

(8)

[wherein, $R^7$ represents a C1-C5 alkyl group or an optionally substituted phenyl group, and X represents a halogen atom] or a compound represented by formula (9):

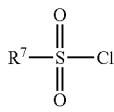

(9)

[wherein, $R^7$ has the same meaning as described above] in place of the compound (2), it is preferable to use the compound (2) in the step (B).

In the reaction of step (B), the at least one of tri (C1-C8 alkyl)amine and alkali metal acetate is used. Among the tri(C1-C8 alkyl)amine and the alkali metal acetate, only the tri(C1-C8 alkyl)amine may be used, only the alkali metal acetate may be used, or both of the tri(C1-C8 alkyl)amine and the alkali metal acetate may be used.

Tri(C1-C8 alkyl)amine is an amine having three (3) of C1-C8 alkyl groups attached to a nitrogen atom thereof, and three (3) of the C1-C8 alkyl groups are independently selected and may be identical to or different from each other.

Examples of the tri(C1-C8 alkyl)amine include trimethylamine, triethylamine, tributylamine, diisopropylethylamine, trioctylamine and a mixture containing two or more thereof, include preferably triethylamine, diisopropylethylamine or trioctylamine, and more preferably triethylamine.

Examples of the alkali metal acetates include lithium acetate, sodium acetate, potassium acetate, cesium acetate and a mixture containing two or more thereof, and include preferably sodium acetate.

Here, in the reaction for preparing the compound (3), it is possible to use pyridines such as pyridine and 2,4,6-trimethylpyridine; imidazoles such as N-methylimidazole, 1,2-dimethylimidazole, 1,4-dimethylimidazole and 1,5-dimethylimidazole; alkali metal carbonates such as lithium carbonate, sodium carbonate, potassium carbonate and cesium carbonate; or alkali metal hydrogen carbonates such as sodium hydrogen carbonate and potassium hydrogen carbonate in place of the tri(C1-C8 alkyl)amine and the alkali metal acetate, and it is preferable to use the at least one of tri(C1-C8 alkyl)amine and alkali metal acetate in the step (B).

An amount of the at least one of tri(C1-C8 alkyl)amine and alkali metal acetate to be used is usually within a range of 1 mol to 10 mol, and preferably 1 mol to 2 mol, per 1 mol of compound (1), but is not limited thereto. A combination of the tri(C1-C8 alkyl)amine and the alkali metal acetate may be used.

The reaction may be carried out in the presence of imidazoles. Examples of the imidazoles include N-methylimidazole, 1,2-dimethylimidazole, 1,4-dimethylimidazole and 1,5-dimethylimidazole, and include preferably N-methylimidazole.

When the reaction is carried out in the presence of imidazoles, an amount thereof to be used is usually within a range of 0.01 mol to 0.2 mol, per 1 mol of compound (1), but is not limited thereto.

The reaction may be carried out in a solvent. Examples of the solvent include ether solvents such as diethyl ether, tetrahydrofuran, tert-butyl methyl ether, cyclopentyl methyl ether and 1,2-dimethoxyethane; hydrocarbon solvents such as pentane, hexane, heptane, octane, benzene, toluene, ethylbenzene, xylene, mesitylene, cyclopentane and cyclohexane; amide solvents such as N-methylpyrrolidone, N,N-dimethylformamide and N,N-dimethylacetamide; and a mixture containing two or more thereof, and include preferably hydrocarbon solvents.

When the reaction is carried out in the solvent, an amount of the solvent to be used is usually within a range of 1 to 20 times by weight as much as an amount of the compound (1), but is not limited thereto.

The compound (1) may be mixed with the above-mentioned solvent in advance and may be used in a form of a solution containing the compound (1).

The tri(C1-C8 alkyl)amine may be used as itself, may be used as a commercially available solution, or may be mixed with the solvent in advance and may be used in a form of a solution containing the same.

The reaction is usually carried out by mixing the compound (1), the compound (2) and at least one of tri(C1-C8 alkyl)amine and alkali metal acetate (hereinafter, also collectively referred to as "the compound such as tri(C1-C8 alkyl)amine"). An order and method of the mixing are not particularly limited, and the examples of the method thereof include a method of adding the compound (1) or the solution of the compound (1) to a mixture of the compound (2) and the compound such as tri(C1-C8 alkyl)amine; a method of adding the compound (2) to a mixture of the compound (1) and the compound such as tri(C1-C8 alkyl)amine; and a method of adding a mixture of the compound (1) and the compound such as tri(C1-C8 alkyl)amine to the compound (2), and preferably include the method of adding the compound (1) or the solution of the compound (1) to the mixture of the compound (2) and the compound such as tri(C1-C8 alkyl)amine; or the method of adding the mixture of the compound (1) and the compound such as tri(C1-C8 alkyl)amine to the compound (2).

When the compound (1) or the solution of the compound (1) is added to the mixture of the compound (2) and the compound such as tri(C1-C8 alkyl)amine, the addition may be carried out at once, or may be carried out portionwise, and it is preferable that the addition is carried out while the addition rate is controlled so that the above-mentioned reaction temperature is maintained.

When the mixture of the compound (1) and the compound such as tri(C1-C8 alkyl)amine is added to the compound (2), the addition may be carried out at once, or may be carried out portionwise, and it is preferable that the addition is carried out while the addition rate is controlled so that the above-mentioned reaction temperature is maintained.

The reaction time is usually within a range of 1 to 96 hours, and preferably 1 to 24 hours, though depending on the conditions such as the reaction temperature. The reaction temperature is 100° C. or higher. The reaction temperature can be within a range of 100° C. to a reflux temperature of the compound (2). The preferable reaction temperature in the case that the compound (2) is an acetic anhydride is as described above.

The compound (3) can be used for the step (C) after concentration under reduced pressure, or can be used as itself without concentration. That is, the compound (3) can be proceeded to the next step of hydrolysis without isolation or purification.

The compound (3) may also be isolated and purified by a conventional method. For example, when a solid is precipitated, the solid formed after the completion of the reaction can be collected by filtration to isolate the compound (3). Further, for example, after the completion of the reaction, the reaction mixture is mixed with water, and extracted with an organic solvent, and the resulting organic layer is then washed, dried, and concentrated under reduced pressure to isolate the compound (3). Here, the organic solvent used for extraction may be an organic solvent in which the compound (3) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as acetone, methyl ethyl ketone and methyl isobutyl ketone; hydrocarbon solvents such as pentane, hexane, heptane, octane, benzene, toluene, ethylbenzene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; and a mixture containing two or more thereof.

In addition, the compound (3) may be further purified by column chromatography, recrystallization and the like.

The step (C) is described below.

In the step (C), the compound (3) is hydrolyzed to obtain the compound (4).

Hydrolysis may be carried out in the presence or absence of an acid or a base.

The compound (4) is one type of pyridone compounds.

As described above, $X^1$ preferably represents a chlorine atom, $X^2$ preferably represents a fluorine atom, and $R^1$ preferably represents a hydrogen atom, and the compound (4) which is defined as the above is referred to as 3-(2-chloro-4-fluorophenoxy)-2(1H)-pyridinone.

Examples of the acid used for hydrolysis include inorganic acids such as hydrochloric acid and sulfuric acid; aliphatic carboxylic acids or halogenated aliphatic carboxylic acids such as acetic acid, propionic acid, butyric acid, hexanoic acid, octanoic acid, 2-ethylhexanoic acid, decanoic acid, dodecanoic acid, chloroacetic acid, dichloroacetic acid, trichloroacetic acid, and trifluoroacetic acid; and organic sulfonic acids such as methanesulfonic acid, trifluoromethanesulfonic acid, 10-camphorsulfonic acid and p-toluenesulfonic acid, and include preferably inorganic acids, aliphatic carboxylic acids or halogenated aliphatic carboxylic acids.

An amount of the acid to be used is usually within a range of 0.01 to 5 mol, and preferably 0.01 to 2 mol, per 1 mol of the compound (3), but is not limited thereto.

Examples of the base used for hydrolysis include alkali metal hydroxides such as lithium hydroxide, sodium hydroxide, potassium hydroxide and cesium hydroxide; and alkaline earth metal hydroxides such as magnesium hydroxide, calcium hydroxide and barium hydroxide, and include preferably sodium hydroxide. The base may be used in a form of an aqueous solution containing the same.

An amount of the base to be used is usually within a range of 2 to 10 mol, per 1 mol of the compound (3), but is not limited thereto.

Water may be used for hydrolysis. An amount of water to be used is usually within a range of 1 to 100 mol, per 1 mol of the compound (3), but is not limited thereto.

The reaction is usually carried out in a solvent. Examples of the solvent include ether solvents such as diethyl ether, tetrahydrofuran, tert-butyl methyl ether, cyclopentyl methyl ether and 1,2-dimethoxyethane; hydrocarbon solvents such as pentane, hexane, heptane, octane, benzene, toluene, ethylbenzene, xylene, mesitylene, cyclopentane and cyclohexane; alcohol solvents such as methanol, ethanol, 1-propanol, 2-propanol and 1-butanol; amide solvents such as N-methylpyrrolidone, N,N-dimethylformamide and N,N-dimethylacetamide; and a mixture containing two or more thereof. Water for hydrolysis may be used as a solvent. In that case, the amount of water to be used may be more than 100 mol per 1 mol of the compound (3).

An amount of the solvent to be used is usually within a range of 0.1 to 20 times by weight as much as the amount of the compound (3), but is not limited thereto.

The reaction temperature is usually within a range of 0° C. to a reflux temperature of the solvent, and is usually within a range of 0 to 100° C. when no solvent other than water is used in the reaction. The reaction time is usually 1 to 72 hours, though depending on the reaction temperature.

After the reaction is completed, the compound (4) can be isolated and purified by a conventional method. For example, when a solid is precipitated, the resulting solid can be collected by filtration to isolate the compound (4). Further, for example, an acid or a base is added to neutralize the reaction mixture, and the mixture then extracted with an organic solvent, and the resulting organic layer is washed, dried, and concentrated under reduced pressure to isolate the compound (4). Here, the organic solvent used for extraction may be a solvent in which the compound (4) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as acetone, methyl ethyl ketone and methyl isobutyl ketone; hydrocarbon solvents such as pentane, hexane, heptane, octane, benzene, toluene, ethylbenzene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; alcohol solvents such as methanol, ethanol, 1-propanol, 2-propanol, 1-butanol; and a mixture containing two or more thereof. In addition, the compound (4) may be further purified by column chromatography, recrystallization and the like.

The compound (4) has a relationship of tautomer with a compound represented by formula (4a):

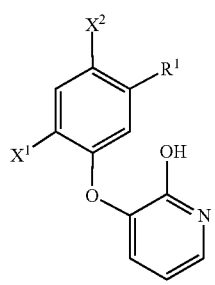

(4a)

[wherein, $X^1$, $X^2$ and $R^1$ have the same meanings as described above]. The tautomer represented by formula (4a) should be also encompassed in the compound (4).

The step (A) is described below.

In the step (A), the compound represented by formula (5) (hereinafter, referred to as "compound (5)") is reacted with the compound represented by formula (6) (hereinafter, referred to as "compound (6)") in the presence of a base to obtain the compound (1).

The reaction is carried out by mixing the compound (5), the compound (6) and the base. When the compound (5), the compound (6) and the base are mixed, an order of mixing is not particularly limited.

An amount of the compound (6) to be used is usually within a range of 0.5 to 10 mol, preferably 1 to 5 mol, and more preferably 1 to 2 mol, per 1 mol of the compound (5), but is not limited thereto.

Examples of the base include alkali metal hydroxides such as lithium hydroxide, sodium hydroxide, potassium hydroxide and cesium hydroxide; alkali metal carbonates such as lithium carbonate, sodium carbonate, potassium carbonate and cesium carbonate; alkali metal phosphates such as trilithium phosphates, trisodium phosphate, tripotassium phosphate and tricesium phosphate; and alkali metal hydrides such as lithium hydride, sodium hydride and potassium hydride, and include preferably alkali metal phosphates.

An amount of the base to be used is usually within a range of 1 to 10 mol, preferably 1 to 5 mol, and more preferably 1 to 2 mol, per 1 mol of the compound (5), but is not limited thereto.

The reaction may be carried out in the presence of additives. Examples of the additives include crown ethers such as 15-crown 5-ether and 18-crown 6-ether, and include preferably 15-crown 5-ether.

When the reaction is carried out in the presence of the additives, an amount thereof to be used is usually within a range of 0.01 to 1 mol, per 1 mol of the compound (5), but is not limited thereto.

The reaction temperature is usually within a range of 95° C. to 180° C., and preferably 140° C. to 160° C. The reaction time is usually within a range of 1 to 72 hours, though depending on the reaction temperature.

The reaction is usually carried out in a solvent. Examples of the solvent include amide solvents such as N-methylpyrrolidone, N,N-dimethylformamide and N,N-dimethylacetamide; sulfoxide solvents such as dimethyl sulfoxide; sulfone solvents such as sulfolane; hydrocarbon solvents such as pentane, hexane, heptane, octane, benzene, toluene, ethylbenzene, xylene, mesitylene, cyclopentane and cyclohexane; halogenated aromatic hydrocarbon solvents such as chlorobenzene and dichlorobenzene; and a mixture containing two or more thereof, include preferably amide solvents, and more preferably N-methylpyrrolidone.

The compound (1) can be isolated and purified by a conventional method. For example, when a solid is precipitated, the solid formed after the completion of the reaction can be collected by filtration to isolate the compound (1). Further, for example, after the completion of the reaction, the reaction mixture is mixed with water, and extracted with an organic solvent, and the resulting organic layer is then washed, dried, and concentrated under reduced pressure to isolate the compound (1). Furthermore, for example, after the completion of the reaction, the reaction mixture is mixed with water, and extracted with an organic solvent, and the resulting organic layer is then mixed with an aqueous solution of a Brønsted acid to obtain an aqueous layer containing the Brønsted acid salt of the compound (1), and the aqueous layer is then neutralized with a base, the compound (1) is extracted as an organic layer with an organic solvent, and the organic layer is, if necessary, washed, dried and concentrated to isolate the compound (1). Here, the organic solvent used for extraction may be an organic solvent in which the compound (1) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as methyl ethyl ketone and methyl isobutyl ketone; hydrocarbon solvents such as pentane, hexane, heptane, octane, benzene, toluene, ethylbenzene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; and a mixture containing two or more thereof. In addition, the compound (1) may be further purified by column chromatography, recrystallization and the like. Alternatively, compound (1) may be used in the step (B) without purification.

The compound (5) can be obtained by reacting a compound represented by formula (7):

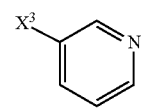

(7)

[wherein, $X^3$ has the same meaning as described above] (hereinafter, referred to as "compound (7)") with an oxidizing agent.

Examples of the oxidizing agent include hydrogen peroxide such as aqueous hydrogen peroxide solution and urea-hydrogen peroxide adduct; peroxy acid such as per-acetic acid and m-chloroperbenzoic acid; and organic peroxide such as tert-butyl hydroperoxide, and include preferably aqueous hydrogen peroxide solution.

A concentration of the aqueous hydrogen peroxide solution is usually within a range of 10 to 70% by weight, and preferably 30 to 60% by weight.

An amount of the oxidizing agent to be used is usually within a range of 1 to 10 mol, preferably 1 to 5 mol, and more preferably 1 to 2 mol, per 1 mol of the compound (7), but is not limited thereto.

The reaction may be carried out in the presence of an acid. Examples of the acid include inorganic acids such as hydrochloric acid and sulfuric acid; sulfonic acids such as methanesulfonic acid and ethanesulfonic acid; and aliphatic carboxylic acids or halogenated aliphatic carboxylic acids such as acetic acid, propionic acid, butyric acid, hexanoic acid, octanoic acid, 2-ethylhexanoic acid, decanoic acid, dodecanoic acid, chloroacetic acid, dichloroacetic acid, trichloroacetic acid and trifluoroacetic acid, and include preferably hydrochloric acid or sulfuric acid.

When the reaction is carried out in the presence of the acid, an amount thereof to be used is usually within a range of 0.01 to 10 mol, and preferably 0.01 to 2 mol, per 1 mol of the compound (7), but is not limited thereto.

The reaction may be carried out in the presence of a metal catalyst. Examples of the metal catalyst include tungsten compounds such as sodium tungstate, sodium tungstate dihydrate, and sodium tungstate decahydrate; vanadium compounds such as sodium orthovanadate (V); and molybdenum compounds such as molybdenum oxide (VI), and include preferably sodium tungstate dihydrate.

When the reaction is carried out in the presence of the metal catalyst, an amount thereof to be used is usually within a range of 0.01 to 1 mol, and preferably 0.01 to 0.1 mol, per 1 mol of the compound (7), but is not limited thereto.

The reaction temperature is usually within a range of 0° C. to 100° C., and preferably 60° C. to 80° C. The reaction time is usually within a range of 1 to 48 hours, though depending on the reaction temperature.

The reaction may be carried out in a solvent which is inert to the reaction, and the examples of the solvent which is inert to the reaction include sulfone solvents such as sulfolane, and water.

The compound (5) can be isolated and purified by a conventional method. For example, when a solid is precipitated, the solid formed after the completion of the reaction can be collected by filtration to isolate the compound (5). Further, for example, after the completion of the reaction, the reaction mixture is mixed with water, and extracted with an organic solvent, and the resulting organic layer is then washed, dried, and concentrated under reduced pressure to isolate the compound (5). Here, the organic solvent used for extraction may be a organic solvent in which the compound (5) is dissolved, and is not particularly limited, and the examples thereof include ether solvents such as diethyl ether, tetrahydrofuran, tert-butyl methyl ether, cyclopentyl methyl ether and 1,2-dimethoxyethane; ester solvents such as methyl acetate, ethyl acetate, propyl acetate, butyl acetate and tert-butyl acetate; ketone solvents such as methyl ethyl ketone and methyl isobutyl ketone; hydrocarbon solvents such as pentane, hexane, heptane, octane, benzene, toluene, ethylbenzene, xylene, mesitylene, cyclopentane and cyclohexane; halogenated hydrocarbon solvents such as dichloromethane, chloroform and carbon tetrachloride; halogenated aromatic hydrocarbon solvents such as chlorobenzene and dichlorobenzene; amide solvents such as N-methylpyrrolidone, N,N-dimethylformamide and N,N-dimethylacetamide; and a mixture containing two or more thereof. In addition, the compound (5) may be further purified by column chromatography, recrystallization and the like. Alternatively, compound (5) may be used for the preparation of compound (1) without purification.

EXAMPLES

Hereinafter, the present invention is described in more detail by using Examples, however, the present invention should not be limited thereto.

Hereinafter, unless otherwise stated, % (percentage) of an aqueous solution containing inorganic salt such as hydrochloric acid, sulfuric acid, sodium hydroxide, sodium sulfite, etc. and a content of a substance mean "% by mass". Unless otherwise stated, "% (percentage) of yield" is based on an amount of substance (mol).

In Examples 1 to 14 and 18 to 34 as well as Comparative Examples 1 to 4 below, unless otherwise stated, quantitative analysis was carried out by high performance liquid chromatography (hereinafter, referred to as "HPLC") according to an absolute calibration method. The analysis conditions are as follows.

[High Performance Liquid Chromatography (HPLC) Analysis Conditions]

Mobile phase: solution A: 0.1% phosphoric acid aqueous solution, solution B: acetonitrile
Gradient conditions: the content of solution B was changed from 30% to 100% over 70 minutes.
Column: XBridge Phenyl, particle size 3.5 μm, 4.6 mm I.D.×15 cm (Nihon Waters K.K.)
UV measurement wavelength: 274 nm
Flow rate: 1.0 mL/min
Column oven temperature: 40° C.

Preparation of 3-(2-chloro-4-fluorophenoxy)-2 (1H)-pyridinone

Example 1

3-(2-Chloro-4-fluorophenoxy)pyridine-N-oxide 1.01 g (content: 76.7%), acetic anhydride 7.67 g and triethylamine 0.38 g were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 8.54 g (content of 2-acetoxy-3-(2-chloro-4-fluorophenoxy)pyridine: 9.55%, yield 78%; content of 3-(2-chloro-4-fluorophenoxy)-2(1H)-pyridinone: 0.94%, yield 9%; total yield 87%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 2

3-(2-Chloro-4-fluorophenoxy)pyridine-N-oxide 1.00 g (content: 76.7%), acetic anhydride 3.84 g and triethylamine 0.37 g were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 4.75 g (content of 2-acetoxy-3-(2-chloro-4-fluorophenoxy)pyridine: 15.6%, yield 72%; content of 3-(2-chloro-4-fluorophenoxy)-2(1H)-pyridinone: 2.14%, yield 11%; total yield 83%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 3

3-(2-Chloro-4-fluorophenoxy)pyridine-N-oxide 1.01 g (content: 76.7%), acetic anhydride 3.85 g, triethylamine 0.37 g and N-methyl-2-pyrrolidone (hereinafter, referred to as "NMP") 76.6 mg were mixed at room temperature, and the mixture was heated to 120° C. and stirred for 7 hours to obtain a mixed solution containing 2-acetoxy-3-(2-chloro-4-fluorophenoxy)pyridine and 3-(2-chloro)-4-fluorophenoxy)-2(1H)-pyridinone 5.02 g (content of 2-acetoxy-3-(2-chloro-4-fluorophenoxy)pyridine: 15.2%, yield 74%; content of 3-(2-chloro-4-fluorophenoxy)-2(1H)-pyridinone: 1.87%, yield 11%; total yield 84%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 4

3-(2-Chloro-4-fluorophenoxy)pyridine-N-oxide 1.00 g (content: 76.7%), acetic anhydride 3.84 g, triethylamine 0.36 g and NMP 0.78 g were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 5.77 g (content of 2-acetoxy-3-(2-chloro-4-fluorophenoxy)pyridine: 13.5%, yield 75%; content of 3-(2-chloro-4-fluorophenoxy)-2(1H)-pyridinone: 1.26%, yield 8%; total yield 83%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 5

3-(2-Chloro-4-fluorophenoxy)pyridine-N-oxide 15.0 g (content: 91.8%), acetic anhydride 68.9 g, triethylamine 6.40 g and N-methylimidazole 0.12 g were mixed at room temperature, and the mixture was heated to 120° C. and stirred for 7 hours to obtain a solution containing 2-acetoxy-3-(2-chloro-4-fluorophenoxy)pyridine and 3-(2-chloro-4-fluorophenoxy)-2(1H)-pyridinone 89.9 g (content of 2-acetoxy-3-(2-chloro-4-fluorophenoxy)pyridine: 15.0%, yield 83%; content of 3-(2-chloro-4-fluorophenoxy)-2(1H)-pyridinone: 0.71%, yield 5%; total yield 88%).

The resulting mixed solution was concentrated under reduced pressure, and xylene 20.7 g, 27% aqueous sodium hydroxide solution 25.6 g and water 13.90 g were added thereto, and the mixture was stirred at 80° C. for 2 hours and 30 minutes, and then separated with a separatory funnel at 80° C. The resulting aqueous layer was cooled to 40° C., and 17% sulfuric acid aqueous solution 24.3 g was added thereto. The resulting mixture was cooled to 15° C. with stirring. The precipitated solid was filtered, and the filtered residue was washed with water 41.4 g. The resulting solid was dried to obtain 3-(2-chloro-4-fluorophenoxy)-2(1H)-pyridinone 12.8 g (content 86.2%, yield 80%).

$^1$H-NMR (400 MHz, DMSO-D$_6$) δ: 12.03 (1H, br s), 7.54 (1H, dd, J=8.4, 2.8 Hz), 7.27 (1H, dd, J=6.6, 2.0 Hz), 7.18-7.13 (2H, m), 6.93 (1H, dd, J=9.0, 4.8 Hz), 6.18 (1H, t, J=6.8 Hz).

Example 6

3-(2-Chloro-4-fluorophenoxy)pyridine-N-oxide 32.6 g (content: 48.0%), acetic anhydride 78.4 g, triethylamine 7.28 g and N-methylimidazole 0.13 g were mixed at room temperature, and the mixture was heated to 120° C. and stirred for 5 hours.

The resulting mixed solution was concentrated under reduced pressure, and xylene 31.5 g, 48% aqueous sodium hydroxide solution 16.3 g and water 78.3 g were added thereto, and the mixture was stirred at 80° C. for 1 hour, and then separated with a separatory funnel at 80° C. As an aqueous layer, an aqueous solution containing 3-(2-chloro-4-fluorophenoxy)-2(1H)-pyridinone 123.8 g (content: 11.8%, yield: 86%) was obtained. The resulting aqueous layer was cooled to 40° C., and 98% sulfuric acid 4.56 g was added thereto, xylene 55.7 g and 1-butanol 10.0 g were further added thereto, and the mixture was stirred at 80° C., and then separated with a separatory funnel at 80° C. The resulting organic layer was washed with water 45.2 g and then cooled to 0° C. The precipitated solid was filtered, and the filtered residue was washed with xylene 45.0 g and subsequently with water 30.1 g, and then dried to obtain 3-(2-chloro-4-fluorophenoxy)-2(1H)-pyridinone 12.5 g (content 91.6%, yield 69%).

Example 7

3-(2-Chloro-4-fluorophenoxy)pyridine-N-oxide 1.00 g (content: 91.8%), acetic anhydride 4.59 g, triethylamine 0.44 g and N-methylimidazole 18.0 mg were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 5.79 g (content of 2-acetoxy-3-(2-chloro-4-fluorophenoxy)pyridine: 15.0%, yield 80%; content of 3-(2-chloro-4-fluorophenoxy)-2(1H)-pyridinone: 1.00%, yield 6%: total yield 86%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 8

3-(2-Chloro-4-fluorophenoxy)pyridine-N-oxide 1.00 g (content: 91.8%), acetic anhydride 4.59 g, triethylamine 0.43 g and potassium acetate 37.8 mg were mixed, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 5.79 g (content of 2-acetoxy-3-(2-chloro-4-fluorophenoxy)pyridine: 15.0%, yield 80%: content of 3-(2-chloro-4-fluorophenoxy)-2(1H)-pyridinone: 0.89%, yield 6%; total yield 86%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 9

3-(2-Chloro-4-fluorophenoxy)pyridine-N-oxide 1.00 g (content: 91.8%), acetic anhydride 4.59 g, triethylamine 0.43 g and sodium acetate 31.1 mg were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 5.79 g (content of 2-acetoxy-3-(2-chloro-4-fluorophenoxy)pyridine: 15.2%, yield 81%; content of 3-(2-chloro-4-fluorophenoxy)-2(1H)-pyridinone: 0.80%, yield 5%; total yield 86%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 10

3-(2-Chloro-4-fluorophenoxy)pyridine-N-oxide 1.00 g (content: 91.8%), acetic anhydride 4.59 g, triethylamine 0.44 g and sodium acetate 63.5 mg are mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 5.77 g (content of 2-acetoxy-3-(2-chloro-4-fluorophenoxy)pyridine: 15.0%, yield 80%; content of 3-(2-chloro-4-fluorophenoxy)-2(1H)-pyridinone: 0.96%, yield 6%; total yield 86%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 11

3-(2-Chloro-4-fluorophenoxy)pyridine-N-oxide 1.00 g (content: 91.8%), acetic anhydride 4.59 g, triethylamine 0.43 g and lithium acetate 25.6 mg were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 5.90 g (content of 2-acetoxy-3-(2-chloro-4-fluorophenoxy)pyridine: 14.9%, yield 82%; content of 3-(2-chloro-4-fluorophenoxy)-2(1H)-pyridinone: 0.68%, yield 4%; total yield 86%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 12

3-(2-Chloro-4-fluorophenoxy)pyridine-N-oxide 1.00 g (content: 91.8%), acetic anhydride 4.59 g and triethylamine 0.44 g were mixed at room temperature, and the mixture was heated to 100° C. and stirred for 25 hours to obtain a mixed solution containing 2-acetoxy-3-(2-chloro-4-fluorophenoxy)pyridine and 3-(2-chloro-4-fluorophenoxy)-2(1H)-pyridinone 5.70 g (content of 2-acetoxy-3-(2-chloro-4-fluorophenoxy)pyridine: 14.1%, yield 75%; content of 3-(2-chloro-4-fluorophenoxy)-2(1H)-pyridinone: 0.86%, yield 5%; total yield 80%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2 (1H)-pyridinone quantitatively.

Example 13

3-(2-Chloro-4-fluorophenoxy)pyridine-N-oxide 1.00 g (content: 91.8%), acetic anhydride 4.59 g and triethylamine 0.43 g were mixed at room temperature, and the mixture is heated to 140° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 5.72 g (content of 2-acetoxy-3-(2-chloro-4-fluorophenoxy)pyridine: 14.9%, yield 79%; content of 3-(2-chloro-4-fluorophenoxy)-2(1H)-pyridinone: 0.84%, yield 5%; total yield 84%).

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Example 14

3-(2-Chloro-4-fluorophenoxy)pyridine-N-oxide 0.50 g (content: 60.5%), acetic anhydride 1.53 g and sodium acetate 0.11 g were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 1.90 g (content of 2-acetoxy-3-(2-chloro-4-fluorophenoxy)pyridine: 12.3%, yield 66%; content of 3-(2-chloro-4-fluorophenoxy)-2(1H)-pyridinone: 2.68%, yield 17%; total yield 83%).

The resulting mixed solution is concentrated under reduced pressure, and xylene 0.45 g, water 0.30 g and 27% aqueous sodium hydroxide solution 0.58 g are added thereto, and the mixture is stirred at 80° C. for 3 hours, and then separated with a separatory funnel at 80° C. The resulting aqueous layer is cooled to 40° C., and 98% sulfuric acid 0.21 g, 1-butanol 0.24 g and xylene 0.96 g are added thereto, and the mixture is separated with a separatory funnel at 80° C. The resulting organic layer is cooled to 40° C., water 0.15 g is added thereto, and the mixture is separated with a separatory funnel at 80° C. The resulting organic layer is cooled to 5° C. with stirring, the precipitated solid is filtered, and the filtered residue is washed with toluene 0.30 g. The resulting solid is dried to obtain 3-(2-chloro-4-fluorophenoxy)-2(1H)-pyridinone quantitatively.

In Examples 15 to 17 below, unless otherwise stated, quantitative analysis was carried out by high performance liquid chromatography (HPLC) according to an internal standard method. The analysis conditions are as follows.
Mobile phase: Solution A: 0.08% ammonium hydrogen carbonate aqueous solution (pH 9.7), Solution B: acetonitrile
Gradient conditions:

TABLE 1

| Time (minute(s)) | Solution A (%) | Solution B (%) |
| --- | --- | --- |
| 0.00 | 90 | 10 |
| 10.00 | 90 | 10 |
| 30.00 | 70 | 30 |
| 40.00 | 70 | 30 |
| 70.00 | 40 | 60 |
| 70.01 | 10 | 90 |
| 80.00 | 10 | 90 |
| 80.01 | 90 | 10 |
| 90.00 | STOP | STOP |

Conditions of powder X-ray diffraction as described herein are as follows.
Powder X-ray diffractometer: SmartLab (produced by Rigaku Corporation)
X-ray output: CuKα, 45 kV, 200 mA
Sampling width: 0.020
Scanning range: 2° to 50°

Example 15

A mixed solution of 3-(2-chloro-4-fluorophenoxy)pyridine-N-oxide 40.3 g (content: 49.6%) and acetic anhydride 100.0 g was added dropwise to triethylamine 17.3 g under reflux over 4 hours, and the mixture was stirred under reflux for 3 hours.

The resulting mixed solution was concentrated under reduced pressure, water 7.5 g was then added thereto, and the mixture was stirred at 80° C. for 2 hours to obtain a solution of 3-(2-chloro-4-fluorophenoxy)-2(1H)-pyridinone 50.0 g (content 33.9%, yield 85%). To the resulting mixed solution, toluene 100.0 g was added dropwise, the mixture was concentrated, and the resulting mixed solution of 3-(2-chloro-4-fluorophenoxy)-2(1H)-pyridinone in toluene and acetic acid 67.5 g (content 26.5%) was heated to 90° C. and then cooled to 15° C. The precipitated solid was filtered, and then the filtered residue was washed with toluene 30.0 g and dried to obtain 3-(2-chloro-4-fluorophenoxy)-2(1H)-pyridinone 12.5 g (content 92.1%, yield 70%) as a crystal. This crystal is referred to as "Crystal A".

Crystal A was a crystal which has diffraction peaks at 2θ=8.3±0.2°, 10.1±0.2°, 11.8±0.2°, 12.7±0.2°, 16.4±0.20, 16.7±0.20, 17.3±0.20, 19.8±0.20, 21.3±0.20, and 23.7±0.2° in the powder X-ray analysis, and the diffraction peaks are shown in Table 2.

TABLE 2

| Value of 2θ (deg) | Relative Intensity (%) |
|---|---|
| 8.3 | 87 |
| 10.1 | 2 |
| 11.8 | 23 |
| 12.7 | 41 |
| 16.4 | 21 |
| 16.7 | 6 |
| 17.3 | 100 |
| 19.8 | 22 |
| 21.3 | 19 |
| 23.7 | 7 |

Example 16

A mixed solution of 3-(2-chloro-4-fluorophenoxy)pyridine-N-oxide 40.0 g (content: 50.0%) and acetic anhydride 100.0 g was added dropwise to triethylamine 17.4 g under reflux over 4 hours, and the mixture was stirred under reflux for 3 hours.

The resulting mixed solution was concentrated under reduced pressure, and xylene 40.0 g and water 4.5 g were added thereto, and the mixture was stirred at 80° C. for 8 hours, and then refluxed with dehydration for 2 hours. The resulting mixed solution was heated to 140° C., and cooled to 15° C., the precipitated solid was filtered, and the filtered residue was washed with xylene 30.0 g, and dried to obtain 3-(2-chloro-4-fluorophenoxy)-2(1H)-pyridinone 17.9 g (content 88.2%, yield 79%) as a crystal. A melting point thereof was 184.8° C. This crystal is referred to as "Crystal B".

Crystal B was a crystal which has diffraction peaks at 2θ=8.3±0.2°, 12.7±0.2°, 16.4±0.2°, 16.7±0.2°, 17.3±0.20, 19.8±0.20, 21.3±0.20, 25.1±0.20, 25.5±0.20, 27.8±0.2° in the powder X-ray analysis, and the diffraction peaks are shown in Table 3.

TABLE 3

| Value of 2θ (deg) | Relative Intensity (%) |
|---|---|
| 8.3 | 100 |
| 12.7 | 47 |
| 16.4 | 22 |
| 16.7 | 8 |
| 17.3 | 92 |
| 19.8 | 24 |
| 21.3 | 12 |
| 25.1 | 18 |
| 25.5 | 20 |
| 27.8 | 33 |

Example 17

N,N-Dimethylformamide 0.1 g was added to 3-(2-chloro-4-fluorophenoxy)-2(1H)-pyridinone 0.04 g, and the resulting slurry solution was shaken at room temperature for 2 days. The resulting crystal was filtered and dried at 60° C. under reduced pressure to obtain 0.03 g of a crystal. A melting point thereof was 185.0° C. This crystal is referred to as "Crystal C".

Crystal C was a crystal which has diffraction peaks at 2θ=10.0±0.2°, 11.8±0.2°, 14.6±0.2°, 18.0±0.2°, 18.5±0.2°, 20.2±0.2°, 21.1±0.2°, 22.7±0.2°, 23.0±0.2°, 23.7±0.2° in the powder X-ray analysis, and the diffraction peaks are shown in Table 4.

TABLE 4

| Value of 2θ (deg) | Relative Intensity (%) |
|---|---|
| 10.0 | 20 |
| 11.8 | 76 |
| 14.6 | 17 |
| 18.0 | 5 |
| 18.5 | 12 |
| 20.2 | 40 |
| 21.1 | 100 |
| 22.7 | 61 |
| 23.0 | 14 |
| 23.7 | 92 |

Preparation of
3-(2-chloro-4-fluorophenoxy)pyridine-N-oxide

Example 18

2-Chloro-4-fluorophenol 1.5 g, 3-chloropyridine-N-oxide 1.6 g, cesium carbonate 4.9 g and dimethylformamide 10 mL were mixed at room temperature, and the mixture was heated to 140° C. and stirred for 20 hours. The resulting reaction mixture was cooled to room temperature, water was added thereto, and the mixture was extracted with chloroform 50 mL. The resulting organic layer was concentrated under reduced pressure, and the residue was purified by silica gel column chromatography to obtain 3-(2-chloro-4-fluorophenoxy)pyridine-N-oxide 1.2 g.

Preparation of 3-(5-amino-2-chloro-4-fluorophenoxy)pyridine-N-oxide

Example 19

5-Amino-2-chloro-4-fluorophenol 3.3 g, 3-chloropyridine-N-oxide 3.1 g, tripotassium phosphate 12.7 g and dimethylformamide 10 mL were mixed at room temperature, and the mixture was heated to 140° C. and stirred for 22 hours. The resulting reaction mixture was cooled to room temperature, water was added thereto, and the mixture was extracted with chloroform 50 mL. The resulting organic layer was concentrated under reduced pressure, and the residue was purified by silica gel column chromatography to obtain 3-(5-amino-2-chloro-4-fluorophenoxy)pyridine-N-oxide 2.2 g.

Preparation of
3-(2-chloro-4-fluorophenoxy)pyridine-N-oxide

Example 20

2-Chloro-4-fluorophenol 1.33 g, a solution of 3-chloropyridine-N-oxide in NMP 2.48 g (content: 42.3%), tripotassium phosphate 2.60 g and NMP 2.11 g were mixed at room temperature, and the mixture was heated to 160° C. and stirred for 24 hours. The resulting reaction mixture was cooled to 80° C., and water was added thereto to obtain a solution of 3-(2-chloro-4-fluorophenoxy)pyridine-N-oxide in NMP 20.3 g (content: 4.69%, yield 49%).

Example 21

2-Chloro-4-fluorophenol 0.77 g, a solution of 3-chloropyridine-N-oxide in NMP 1.50 g (content: 40.7%), trisodium phosphate 1.16 g and NMP 1.22 g were mixed at room temperature, and the mixture was heated to 160° C. and stirred for 24 hours. The resulting reaction mixture was cooled to 80° C., and water was added thereto to obtain a solution of 3-(2-chloro-4-fluorophenoxy)pyridine-N-oxide in NMP 11.1 g (content: 4.15%, yield 39%).

Example 22

2-Chloro-4-fluorophenol 0.77 g, a solution of 3-chloropyridine-N-oxide in NMP 1.50 g (content: 40.7%), trisodium phosphate 1.16 g, NMP 1.22 g and 15-crown 5-ether 1.58 g were mixed at room temperature, and the mixture was heated to 160° C. and stirred for 24 hours. The resulting reaction mixture was cooled to 80° C., and water was added thereto to obtain a solution of 3-(2-chloro-4-fluorophenoxy) pyridine-N-oxide in NMP 11.5 g (content: 4.51%, yield 45%).

Example 23

2-Chloro-4-fluorophenol 0.53 g, a solution of 3-chloropyridine-N-oxide in NMP 1.07 g (content: 42.3%), tripotassium phosphate 1.04 g and NMP 0.85 g were mixed at room temperature, and the mixture was heated to 170° C. and stirred for 32 hours. The resulting reaction mixture was cooled to 80° C., and water was added thereto to obtain a solution of 3-(2-chloro-4-fluorophenoxy)pyridine-N-oxide in NMP 17.95 g (content: 2.42%, yield 55%).

Example 24

2-Chloro-4-fluorophenol 0.53 g, a solution of 3-chloropyridine-N-oxide in NMP 1.01 g (content: 42.3%), potassium carbonate 0.94 g and NMP 0.85 g were mixed at room temperature, and the mixture was heated to 170° C. and stirred for 32 hours. The resulting reaction mixture was cooled to 80° C., and water was added thereto to obtain a solution of 3-(2-chloro-4-fluorophenoxy)pyridine-N-oxide in NMP 15.7 g (content: 2.03%, yield 41%).

Example 25

2-Chloro-4-fluorophenol 0.53 g, a solution of 3-chloropyridine-N-oxide in NMP 1.51 g (content: 40.7%), cesium carbonate 2.30 g and NMP 1.22 g were mixed at room temperature, and the mixture was heated to 160° C. and stirred for 24 hours. The resulting reaction mixture was cooled to 80° C., and water was added thereto to obtain a solution of 3-(2-chloro-4-fluorophenoxy)pyridine-N-oxide in NMP 17.7 g (content: 3.34%, yield 52%).

Example 26

2-Chloro-4-fluorophenol 0.57 g, a solution of 3-fluoropyridine-N-oxide in NMP 1.51 g (content: 27.0%), tripotassium phosphate 1.12 g and NMP 0.81 g were mixed at room temperature, and the mixture was heated to 160° C. and stirred for 16 hours. The resulting reaction mixture was cooled to 80° C., and water was added thereto to obtain a solution of 3-(2-chloro-4-fluorophenoxy)pyridine-N-oxide in NMP 11.27 g (content: 5.32%, yield 70%).

Preparation of 3-(5-amino-2-chloro-4-fluorophenoxy)pyridine-N-oxide

Example 27

5-Amino-2-chloro-4-fluorophenol 23.4 g, a solution of 3-chloropyridine-N-oxide in NMP 42.6 g (content: 47.6%), tripotassium phosphate 43.3 g and NMP 17.7 g were mixed at room temperature, and the mixture was heated to 160° C. and stirred for 24 hours. The resulting reaction mixture was cooled to 80° C., and water 123.4 g was added thereto to obtain a solution of 3-(5-amino-2-chloro-4-fluorophenoxy) pyridine-N-oxide in NMP 244.9 g. The resulting solution was analyzed by HPLC, and thereby it was confirmed that 3-(5-amino-2-chloro-4-fluorophenoxy)pyridine-N-oxide was obtained in the solution of NMP in 52% yield.

Example 28

5-Amino-2-chloro-4-fluorophenol 0.64 g, a solution of 3-fluoropyridine-N-oxide in NMP 1.50 g (content: 27.0%), tripotassium phosphate 1.12 g and NMP 0.81 g were mixed at room temperature, and the mixture was heated to 160° C. and stirred for 16 hours. The resulting reaction solution was cooled to 80° C., and water was added thereto to obtain of a solution of 3-(5-amino-2-chloro-4-fluorophenoxy)pyridine-N-oxide in NMP 14.09 g. The resulting solution was analyzed by HPLC, and thereby it was confirmed that 3-(5-amino-2-chloro-4-fluorophenoxy)pyridine-N-oxide was obtained in the solution of NMP in 64% yield.

Preparation of 3-(2-chloro-4-fluorophenoxy)-2 (1H)-pyridinone

Example 29

3-(2-Chloro-4-fluorophenoxy)pyridine-N-oxide 0.50 g (content: 60.5%), acetic anhydride 1.21 g and triethylamine 0.14 g were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 1.84 g (content of 2-acetoxy-3-(2-chloro-4-fluorophenoxy)pyridine: 12.7%, yield 70%; content of 3-(2-chloro-4-fluorophenoxy)-2(1H)-pyridinone: 1.04%, yield 6%; total yield 76%).

The resulting mixed solution is concentrated under reduced pressure, and xylene 0.77 g, water 1.92 g and 27% aqueous sodium hydroxide solution 0.71 g are added thereto, and the mixture is stirred at 80° C. for 3 hours, and then separated with a separatory funnel at 80° C. The resulting aqueous layer is cooled to 40° C., and 98% sulfuric acid 0.24 g, 1-butanol 0.31 g and xylene 0.39 g are added thereto, and the mixture is separated with a separatory funnel at 80° C. The resulting organic layer is cooled to 40° C., water 1.15 g is added thereto, and the mixture is separated with a separatory funnel at 80° C. The resulting organic layer is cooled to 5° C. with stirring, the precipitated solid is filtered, and the filtered residue is washed with toluene 0.77 g. The resulting solid is dried to obtain 3-(2-chloro-4-fluorophenoxy)-2(1H)-pyridinone quantitatively.

Example 30

3-(2-Chloro-4-fluorophenoxy)pyridine-N-oxide 0.50 g (content: 60.5%), acetic anhydride 1.52 g and diisopropylethylamine 0.18 g were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 2.19 g (content of 2-acetoxy-3-(2-chloro-4-fluorophenoxy)pyridine: 10.5%, yield 77%; content of 3-(2-chloro-4-fluorophenoxy)-2(1H)-pyridinone: 0.83%, yield 6%; total yield 83%).

The resulting mixed solution is concentrated under reduced pressure, and xylene 0.77 g, water 1.92 g and 27% aqueous sodium hydroxide solution 0.71 g are added thereto, and the mixture is stirred at 80° C. for 3 hours, and then separated with a separatory funnel at 80° C. The resulting aqueous layer is cooled to 40° C., and 98% sulfuric acid 0.24 g, 1-butanol 0.31 g and xylene 0.39 g are added thereto, and the mixture is separated with a separatory funnel at 80° C. The resulting organic layer is cooled to 40° C., water 1.15 g is added thereto, and the mixture is separated with a separatory funnel at 80° C. The resulting organic layer is cooled to 5° C. with stirring, the precipitated solid is filtered, and the filtered residue is washed with toluene 0.77 g. The resulting solid is dried to obtain 3-(2-chloro-4-fluorophenoxy)-2(1H)-pyridinone quantitatively.

Example 31

3-(2-Chloro-4-fluorophenoxy)pyridine-N-oxide 0.50 g (content: 60.5%), acetic anhydride 1.51 g and trioctylamine 0.49 g were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 2.49 g (content of 2-acetoxy-3-(2-chloro-4-fluorophenoxy)pyridine: 9.22%, yield 77%; content of 3-(2-chloro-4-fluorophenoxy)-2(1H)-pyridinone: 1.13%, yield 9%; total yield 86%).

The resulting mixed solution is concentrated under reduced pressure, and xylene 0.77 g, water 1.92 g and 27% aqueous sodium hydroxide solution 0.71 g are added thereto, and the mixture is stirred at 80° C. for 3 hours, and then separated with a separatory funnel at 80° C. The resulting aqueous layer is cooled to 40° C., and 98% sulfuric acid 0.24 g, 1-butanol 0.31 g and xylene 0.39 g are added thereto, and the mixture is separated with a separatory funnel at 80° C. The resulting organic layer is cooled to 40° C., water 1.15 g is added thereto, and the mixture is separated with a separatory funnel at 80° C. The resulting organic layer is cooled to 5° C. with stirring, the precipitated solid is filtered, and the filtered residue is washed with toluene 0.77 g. The resulting solid is dried to obtain 3-(2-chloro-4-fluorophenoxy)-2(1H)-pyridinone quantitatively.

Preparation of 3-(5-acetylamino-2-chloro-4-fluorophenoxy)-2(1H)-pyridinone and 3-(5-amino-2-chloro-4-fluorophenoxy)-2 (1H)-pyridinone Example 32

3-(5-Amino-2-chloro-4-fluorophenoxy)pyridine-N-oxide 2.0 g (content: 97.8%), acetic anhydride 10.7 g, triethylamine 1.72 g and N-methylimidazole 0.02 g are mixed at room temperature, and the mixture is heated to 120° C. and stirred for 8 hours. The resulting reaction mixture is concentrated, and xylene 4.1 g, water 9.7 g and 27% aqueous sodium hydroxide solution 3.4 g are added thereto, and the mixture is stirred at room temperature for 8 hours. To the resulting mixture, 27% aqueous sodium hydroxide solution 3.4 g is added, and the mixture is stirred at room temperature for 8 hours. At room temperature, concentrated hydrochloric acid 3.2 g and subsequently ethyl acetate 9.8 g are added thereto, the mixture is heated to 60° C., and ethanol 1.0 g is added thereto. The precipitated solid is filtered, and the resulting filtered residue is washed with water 10.5 g and subsequently with ethyl acetate 9.6 g, and dried to obtain a mixture of 3-(5-acetylamino-2-chloro-4-fluorophenoxy)-2(1H)-pyridinone and 3-(5-amino-2-chloro-4-fluorophenoxy)-2(1H)-pyridinone.

Preparation of 3-(2-chloro-4-fluorophenoxy)-2 (1H)-pyridinone

Example 33

A solution of 3-chloropyridine-N-oxide in NMP 105.9 g (content: 40.7%), 2-chloro-4-fluorophenol 48.5 g, tripotassium phosphate 79.2 g and NMP 20.7 g were mixed at room temperature, and the mixture was heated to 160° C. and stirred for 25 hours. The resulting reaction mixture was cooled to 50° C., water was added thereto, and the mixture was separated with a separatory funnel to obtain a solution of 3-(2-chloro-4-fluorophenoxy)pyridine-N-oxide in NMP (content 19.7%) 222.2 g as an organic layer.

To a solution 180.0 g which was a part of the resulting solution of 3-(2-chloro-4-fluorophenoxy)pyridine-N-oxide in NMP (content 19.7%), saturated saline 32.9 g was added at room temperature, the mixture was extracted 5 times with xylene 164.7 g at 80° C., and the resulting organic layer was concentrated to obtain a solution of 3-(2-chloro-4-fluorophenoxy)pyridine-N-oxide in NMP 87.5 g (content: 36.6%, yield 50%).

A solution 81.0 g which was a part of the resulting solution of 3-(2-chloro-4-fluorophenoxy)pyridine-N-oxide in NMP (content: 36.6%), acetic anhydride 148.4 g, triethylamine 13.8 g and N-methylimidazole 0.25 g were mixed, the mixture was heated to 120° C. and stirred for 7 hours.

The resulting reaction mixture was concentrated under reduced pressure, and xylene 44.5 g, 27% aqueous sodium hydroxide solution 54.7 g and water 29.8 g were added thereto, and the mixture was stirred at 80° C., and then separated with a separatory funnel at 80° C. to obtain an aqueous solution of 3-(2-chloro-4-fluorophenoxy)-2(1H)-pyridinone 223.2 g (content 11.2%, yield 83%) as an aqueous layer. The resulting aqueous layer was cooled to 40° C., 44% sulfuric acid 24.2 g was added thereto, and then the mixture was cooled to 15° C. with stirring. The precipitated solid was filtered, and the filtered residue was washed with water 59.2 g. The resulting solid was dried to obtain 3-(2-chloro-4-fluorophenoxy)-2(1H)-pyridinone 46.3 g (content 52.4%, yield 82%).

Preparation of 3-(2-chloro-4-fluorophenoxy)pyridine-N-oxide

Example 34

3-Chloropyridine 200.2 g, water 31.3 g, sodium tungstate dihydrate 5.9 g and 98% concentrated sulfuric acid 14.1 g were mixed at room temperature, and the mixture was heated to 60° C. To the mixture kept at 60° C., 30% aqueous hydrogen peroxide solution 217.5 g was added dropwise over 11 hours. The mixture was stirred at 60° C. overnight, cooled to 35° C., and 22% aqueous sodium sulfite solution 300.8 g, 48% aqueous sodium hydroxide solution 102.2 g and NMP 197.9 g were added thereto, and the resulting mixture was separated with a separatory funnel to obtain an organic layer containing 3-chloropyridine-N-oxide 647.8 g (content: 30.0%, yield: 85%). To an organic layer 633.6 g which was a part of the resulting organic layer, xylene 191.5 g was added, and the mixture was subjected to a dehydration under reflux using a Dean-Stark apparatus to obtain a solution of 3-chloropyridine-N-oxide in NMP 358.4 g (content: 46.0%).

A solution 100.3 g which was a part of the resulting solution of 3-chloropyridine-N-oxide in NMP, 2-chloro-4-fluorophenol 57.9 g, trisodium phosphate 86.5 g, NMP 59.6 g and 15-crown 5-ether 11.54 g were mixed at room temperature, the mixture was stirred at 160° C. for 165 hours. The resulting reaction mixture was cooled to 80° C., water was added thereto, and the mixture was separated with a separatory funnel to obtain a solution of 3-(2-chloro-4-fluorophenoxy)pyridine-N-oxide in NMP (content 13.6%, yield 71%) as an organic layer and an aqueous solution of 3-(2-chloro-4-fluorophenoxy)pyridine-N-oxide (content 0.1%, yield 0.1%) as an aqueous layer. To the resulting organic layer, saturated saline 46 g was added, and the mixture was extracted 3 times with xylene 226 g. The resulting organic layer was concentrated to obtain a solution of 3-(2-chloro-4-fluorophenoxy)pyridine-N-oxide 121.9 g (content: 45.4%, yield 66%).

Comparative Example 1 (as an Example in which a Tri(C1-C8 Alkyl)Amine and an Alkali Metal Acetate were not Used)

3-(2-Chloro-4-fluorophenoxy)pyridine-N-oxide 1.0 g and acetic anhydride 5.0 g were mixed at room temperature, and the mixture was heated to 120° C. and stirred for 8.5 hours. The resulting reaction mixture was concentrated under reduced pressure to obtain a concentrated solution 4.7 g. To a solution 2.9 g which was a part of the resulting concentrated solution, concentrated hydrochloric acid 6.1 g was added, and the mixture was heated at 100° C. for 2 hours to obtain a mixed solution containing 3-(2-chloro-4-fluorophenoxy)-2(1H)-pyridinone 5.3 g (content 7.7%, yield 65%).

Comparative Example 2 (as an Example in which the Amount of the Compound (2) Used in the Step (B) was Two (2) Times by Weight as Much as the Amount of the Compound (1))

3-(2-Chloro-4-fluorophenoxy)pyridine-N-oxide 1.01 g (content: 76.7%), acetic anhydride 1.51 g, triethylamine 0.42 g and toluene 1.59 g were mixed at room temperature, and the mixture was heated to 120° C. and stirred for 8 hours to obtain a mixed solution containing 2-acetoxy-3-(2-chloro-4-fluorophenoxy)pyridine and 3-(2-chloro-4-fluorophenoxy)-2(1H)-pyridinone 4.35 g (content of 2-acetoxy-3-(2-chloro-4-fluorophenoxy)pyridine: 12.2%, yield 51%; content of 3-(2-chloro-4-fluorophenoxy)-2(1H)-pyridinone: 2.07%, yield 10%; total yield 61%).

It was confirmed that a compound represented by formula (A):

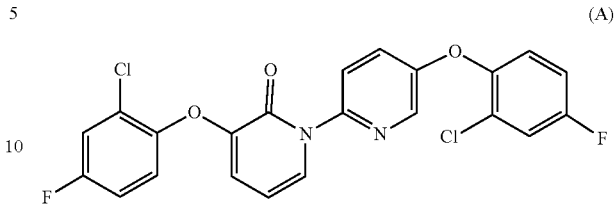

(A)

as a main impurity (hereinafter, referred to as "Impurity A") was produced with an area percentage of 18% of high performance liquid chromatography.

The resulting mixed solution is concentrated under reduced pressure, and xylene 1.53 g, water 3.84 g and 27% aqueous sodium hydroxide solution 1.42 g are added thereto, and the mixture is stirred at 80° C. for 3 hours, and then separated with a separatory funnel at 80° C. The resulting aqueous layer is cooled to 40° C., and 98% sulfuric acid 0.48 g, 1-butanol 0.61 g and xylene 0.77 g are added thereto, and the mixture is separated with a separatory funnel at 80° C. The resulting organic layer is cooled to 40° C., water 2.30 g is added thereto, and the mixture is separated with a separatory funnel at 80° C. The resulting organic layer is cooled to 5° C. with stirring, the precipitated solid is filtered, and the filtered residue is washed with toluene 1.53 g. The resulting solid is dried to obtain 3-(2-chloro-4-fluorophenoxy)-2(1H)-pyridinone quantitatively.

Analytical values of the impurity A are described below.
HRMS: [M+H]$^+$=461.0265, $C_{22}H_{13}Cl_2F_2N_2O_3$ $^1$H-NMR (CDCl$_3$, 300 MHz, δ/ppm): 6.23 (t, J=7.2 Hz, 1H), 6.83 (dd, J=7.5, 1.8 Hz, 1H), 6.91-7.15 (m, 4H), 7.20 (dd, J=8.0, 3.0 Hz, 1H), 7.25-7.32 (m, 2H), 7.70 (dd, J=7.2, 1.8 Hz, 1H), 7.95 (d, J=8.7 Hz, 1H), 8.24 (d, J=3.0 Hz, 1H). $^{13}$C-NMR (CDCl$_3$, 75 MHz, δ/ppm): 104.7, 114.7 (d, J=22.7 Hz), 115.4 (d, J=22.7 Hz), 117.9 (d, J=33.0 Hz), 118.3 (d, J=33.0 Hz), 120.8 (d, J=8.8 Hz), 122.2, 122.4, 123.0 (d, J=8.8 Hz), 125.1, 126.1 (d, J=10.3 Hz), 127.5 (d, J=11.0 Hz), 130.9, 137.8, 146.0, 147.0 (d, J=2.0 Hz), 147.2, 147.9 (d, J=3.7 Hz), 153.5, 157.3, 158.7 (d, J=244.7 Hz), 159.4 (d, J=246.9 Hz).

Comparative Example 3 (as an Example in which the Amount of the Compound (2) Used in the Step (B) was Three (3) Times by Weight as Much as the Amount of the Compound (1))

3-(2-Chloro-4-fluorophenoxy)pyridine-N-oxide 0.50 g (content: 60.5%), acetic anhydride 0.91 g and triethylamine 0.14 g were mixed at room temperature, and the mixture was heated to 120° C. and stirred for 7 hours to obtain a mixed solution containing 2-acetoxy-3-(2-chloro-4-fluorophenoxy)pyridine and 3-(2-chloro-4-fluorophenoxy)-2(1H)-pyridinone 1.54 g (content of 2-acetoxy-3-(2-chloro-4-fluorophenoxy)pyridine: 12.9%, yield 60%; content of 3-(2-chloro-4-fluorophenoxy)-2(1H)-pyridinone: 0.79%, yield 4%; total yield 64%).

The resulting mixed solution is concentrated under reduced pressure, and xylene 0.77 g, water 1.92 g and 27% aqueous sodium hydroxide solution 0.71 g are added thereto, and the mixture is stirred at 80° C. for 3 hours, and then separated with a separatory funnel at 80° C. The resulting aqueous layer is cooled to 40° C., and 98% sulfuric acid 0.24 g, 1-butanol 0.31 g and xylene 0.39 g are added thereto, and the mixture is separated with a separatory funnel at 80° C. The resulting organic layer is cooled to 40° C., water 1.15 g is added thereto, and the mixture is separated with a separatory funnel at 80° C. The resulting organic layer is cooled to 5° C. with stirring, the precipitated solid is filtered, and the filtered residue is washed with toluene 0.77 g. The resulting solid is dried to obtain 3-(2-chloro-4-fluorophenoxy)-2(1H)-pyridinone quantitatively.

Comparative Example 4 (as an Example in which the Reaction Temperature in the Step (B) was 90° C.)

3-(2-Chloro-4-fluorophenoxy)pyridine-N-oxide 0.50 g (content: 60.5%), acetic anhydride 1.51 g and triethylamine 0.14 g were mixed at room temperature, and the mixture was heated to 90° C. and stirred for 48 hours to obtain a mixed solution containing 2-acetoxy-3-(2-chloro-4-fluorophenoxy)pyridine and 3-(2-chloro-4-fluorophenoxy)-2(1H)-pyridinone 2.13 g (content of 2-acetoxy-3-(2-chloro-4-fluorophenoxy)pyridine: 8.13%, yield 58%; content of 3-(2-chloro-4-fluorophenoxy)-2(1H)-pyridinone: 0.99%, yield 7%; total yield 65%).

The resulting mixed solution is concentrated under reduced pressure, and xylene 0.77 g, water 1.92 g and 27% aqueous sodium hydroxide solution 0.71 g are added thereto, and the mixture is stirred at 80° C. for 3 hours, and then separated with a separatory funnel at 80° C. The resulting aqueous layer is cooled to 40° C., and 98% sulfuric acid 0.24 g, 1-butanol 0.31 g and xylene 0.39 g are added thereto, and the mixture is separated with a separatory funnel at 80° C. The resulting organic layer is cooled to 40° C., water 1.15 g is added thereto, and the mixture is separated with a separatory funnel at 80° C. The resulting organic layer is cooled to 5° C. with stirring, the precipitated solid is filtered, and the filtered residue is washed with toluene 0.77 g. The resulting solid is dried to obtain 3-(2-chloro-4-fluorophenoxy)-2(1H)-pyridinone quantitatively.

INDUSTRIAL APPLICABILITY

The present invention provides a method for preparing the compound (4), which is useful as an intermediate for producing herbicides.

The invention claimed is:
1. A method for preparing a compound represented by formula (4):

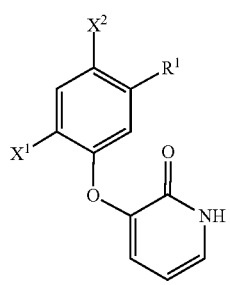

(4)

[wherein, $X^1$ and $X^2$ each independently represent a halogen atom, $R^1$ represents a hydrogen atom, an amino group or a group represented by $NHCOR^2$, and $R^2$ represents a C1-C5 alkyl group]

which comprises a step (B): a step of reacting a compound represented by formula (1):

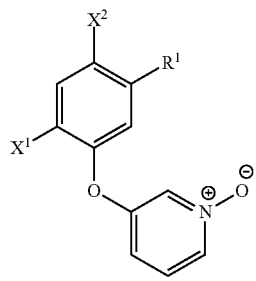

(1)

[wherein, $X^1$, $X^2$ and $R^1$ have the same meanings as described above]
with a compound represented by formula (2):

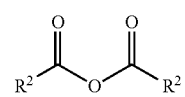

(2)

[wherein, $R^2$ has the same meaning as described above]
which is 4 to 10 times by weight as much as the compound represented by formula (1), in the presence of at least one of a tri(C1-C8 alkyl)amine and an alkali metal acetate at a temperature of 100° C. or higher to obtain a compound represented by formula (3):

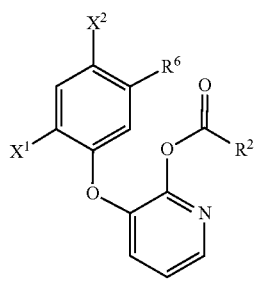

(3)

[wherein, $X^1$, $X^2$ and $R^2$ have the same meanings as described above, and $R^6$ represents a hydrogen atom or a group represented by $NHCOR^2$]; and
a step (C): a step of hydrolyzing the compound represented by formula (3) to obtain the compound represented by formula (4).

2. The method according to claim 1, wherein the tri(C1-C8 alkyl)amine is triethylamine, diisopropylethylamine or trioctylamine.

3. The method according to claim 1, wherein the alkali metal acetate is sodium acetate.

4. The method according to claim 1, wherein the at least one of tri(C1-C8 alkyl)amine and alkali metal acetate includes a tri(C1-C8 alkyl)amine.

5. The method according to claim 1, wherein the at least one of tri(C1-C8 alkyl)amine and alkali metal acetate includes an alkali metal acetate.

6. The method according to claim 4, wherein the tri(C1-C8 alkyl)amine is triethylamine, diisopropylethylamine or trioctylamine.

7. The method according to claim 5, wherein the alkali metal acetate is sodium acetate.

8. A method for preparing a compound represented by formula (4):

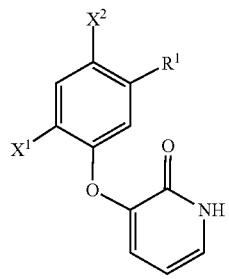
(4)

[wherein, $X^1$ and $X^2$ each independently represent a halogen atom, $R^1$ represents a hydrogen atom, an amino group or a group represented by NHCOR$^2$, and $R^2$ represents a C1-C5 alkyl group]

which comprises a step (A) and the step (B) and the step (C) described in claim 1:

step (A): a step of reacting a compound represented by formula (5):

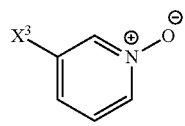
(5)

[wherein, $X^3$ represents a halogen atom]

with a compound represented by formula (6):

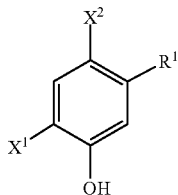
(6)

[wherein, $X^1$, $X^2$ and $R^1$ have the same meanings as described above]
in the presence of a base to obtain a compound represented by formula (1) in claim 1.

9. The method according to claim 1, wherein $X^1$ represents a chlorine atom.

10. The method according to claim 1, wherein $X^2$ represents a fluorine atom.

11. A compound represented by formula (3):

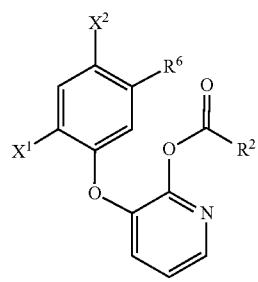
(3)

[wherein, $X^1$ and $X^2$ each independently represent a halogen atom, $R^2$ represents a C1-C5 alkyl group, and $R^6$ represents a hydrogen atom or a group represented by NHCOR$^2$].

* * * * *